US006861507B1

(12) United States Patent
Ala'Aldeen et al.

(10) Patent No.: US 6,861,507 B1
(45) Date of Patent: Mar. 1, 2005

(54) SCREENING OF NEISSERIAL VACCINE CANDIDATES AND VACCINES AGAINST PATHOGENIC NEISSERIA

(75) Inventors: Dlawer Ala'Aldeen, Nottingham (GB); Ian Todd, Nottingham (GB)

(73) Assignee: University of Nottingham, Nottingham (GB)

( * ) Notice: Subject to any disclaimer, the term of this patent is extended or adjusted under 35 U.S.C. 154(b) by 0 days.

(21) Appl. No.: 09/743,674

(22) PCT Filed: Jul. 9, 1999

(86) PCT No.: PCT/GB99/02205

§ 371 (c)(1),
(2), (4) Date: Jan. 10, 2001

(87) PCT Pub. No.: WO00/03003

PCT Pub. Date: Jan. 20, 2000

(30) Foreign Application Priority Data

Jul. 10, 1998 (GB) .............................................. 9814902

(51) Int. Cl.$^7$ .......................... C07K 1/00; A61K 39/02; A61K 39/095; A61K 39/00
(52) U.S. Cl. .................... 530/350; 530/825; 424/190.1; 424/234.1; 424/250.1; 424/184.1; 514/2
(58) Field of Search ........................... 424/234.1, 249.1, 424/250.1, 184.1, 93.4, 190.1; 530/350, 825; 514/2, 898, 921

(56) References Cited

FOREIGN PATENT DOCUMENTS

| EP | 0 287 206 | | 10/1988 |
|---|---|---|---|
| WO | WO 90/06696 | * | 6/1990 |

OTHER PUBLICATIONS

Ellis RW. Vaccines. (Eds) Plotkin et al. W.B. Sanunders Company, Philadelphia, Chapter 29, 1988.*
International Preliminary Examination Report, International Application No. PCT/GB99/02205, dated Oct. 6, 2000.
WO 99 24578 A (Pizza Mariagrazia; Scarlato Vincenzo (IT); Rappuoli Rino (IT); CHI) May 20, 1999.
Wiertz c J et al: T–cell responses to outer membrane proteins of Neisseria meningtidis:comparative study of the Opa, Opc, and PorA proteins. Infection and Immunity, (Jan. 1996) 64 (1) 298–304.
Kizil G et al: Identifiction and characterization of TspA, a major CD4(+)T–cell—and B–cell –stimulating Neisseria–specific antigen. Infection and Immunity, (Jul. 1999) 67 (7) 3533–41.
Naess L M et al: Human T–cell responses after vaccination with the Norwegian group B meningococcal outer membrane vesicle vaccine. Infection and Immunity. (Mar. 1998) 66 (3) 959–65.
Sanderson, S et al. J. Exp. Med. 1995. vol. 182, pp 1751–1757.
PCT International Application Published, WO/00/03003, Publication Date: Jan. 20, 2000.

* cited by examiner

*Primary Examiner*—S. Devi
(74) *Attorney, Agent, or Firm*—Watts Hoffman Co., L.P.A.

(57) ABSTRACT

Methods of screening for vaccine candidates, vaccines against pathogenic *neisscria* and intermediaries for such vaccines have been developed. Two vaccine candidates TspA and TspB have been identified and characterised which either alone or in conjunction with the vaccines provide for treatment against pathogenic *neisserias* in particular *Neisseria meningitidis* and/or *Neisseria gonorrhoea*.

2 Claims, 1 Drawing Sheet

SCREENING OF NEISSERIAL VACCINE CANDIDATES AND VACCINES AGAINST PATHOGENIC NEISSERIA

The instant application is a national stage 371 application of PCT/GB99/02205 having an International Filing Date of Jul. 9, 1999 and claims priority from United Kingdom Application Number 9814902.4, filed Jul. 10, 1998.

The present invention relates to vaccines for Pathogenic *Neisseria*, and particularly but not exclusively to a screening system for the identification of CD4+ T-cell stimulating vaccines in Pathogenic *Neisseria*.

SUMMARY OF THE DISCLOSURE

The term "vaccine candidates" is used to refer to peptides which may prove, upon further study, to exhibit some form of vaccine property. In particular, the vaccine candidates discussed below are peptides which stimulate CD4+ T-cells (T-cells with CD4 marker on them).

The generic name Pathogenic *Neisseria* covers the pathogenic organisms *Neisseria meningitidis* and *Neisseria gonorrhoea*.

*Neisseria meningitidis* (the meningococcus) causes meningitis and overwhelming septicaemia that can kill within hours. It also causes outbreaks of meningococcal disease. *Neisseria gonorrhoea* (the gonococcus) causes gonorrhoea and other invasive diseases, e.g. pelvic inflammatory diseases and septic arthritis.

Although the two neisserial species (*N. meningitidis* and *N. gonorrhoea*) have evolved to colonise and invade different anatomical sites of the human body, they are strongly related and share extensive amount of genetic, immunochemical and other biological properties. They are believed to have evolved from a common ancestor, a view strongly supported by the recently released respective genomic sequence data. The outer membrane structure of the two organisms are very similar with a vast number of outer membrane proteins, including some vaccine candidates, being virtually identical. Recent data suggest that vaccines based on conserved (cross-reactive) immunogenic proteins may protect against both organisms.

The mechanisms responsible for the development of natural immunity to meningococcal disease remain unclear and the currently available capsular polysaccharide (CPS)-based vaccines provide only serogroup-specific and short-lived protection and are not effective in children under two years of age. Additionally, the CPS of serogroup B meningococci, which are responsible for the majority of cases in Europe and America, is only very poorly immunogenic in humans, generating mainly IgM antibodies.

Recovery from meningococcal infection is followed by long lasting immunity and, in the absence of immunodeficiencies, second episodes of meningitis (with homologous or heterologous strains) are extremely rare. This fact indicates that there are non-capsular (cross-reactive) antigens that can stimulate T-cell memory and thus generate a long-lasting and cross-protective immunity.

To achieve an efficient humoral immune response resulting in the production of high affinity IgG antibodies and the generation of memory B lymphocytes (B-cells), help from T lymphocytes (T-cells) is required. However, helper T-cells respond to peptide antigens associated with class II molecules of the major histocompatibility complex (MHC—designated HLA in humans) on the surface of antigen presenting cells. Therefore, they will not be stimulated by purified polysaccharide vaccines (T-cell independent B-cell immunogens). To trigger a strong memory T-cell response when the host confronts the virulent organism, the target B-cell epitope should be expressed along with helper T-cell stimulating epitopes. Identification and characterisation of the peptide epitopes that can best stimulate meningococcal specific $CD4^+$T-cells is an important part of the present invention. An ideal meningococcal vaccine must consist of a carefully selected mixture of well-characterised B- and T-cell antigens capable of generating a long lasting immunity.

It appears that meningococcal vaccine candidates will also have the potential to protect against gonococcal disease.

In the following description the term T-cell clone is defined as the population of cells which originate from a single T cell.

In a first aspect the present invention provides a method of generating T-cell lines and clones specific to neisserial proteins, the method comprising isolating peripheral blood mononuclear cells (PBMCs) from the peripheral blood of normal donors and patients recovering from neisserial disease, culturing the PBMCs with neisserial proteins with or without a proliferation stimulant for a prescribed period, stimulating proliferation of T-cell lines and clones which are specific to neisserial proteins, and maintaining same by regular stimulation.

The neisserial proteins are preferably prepared from *Neisseria meningitidis* and/or *Neisseria gonorrhoea* grown under iron restrictions to induce the expression of iron-regulated proteins.

The peripheral blood is preferably obtained from naturally infected patients at different stages of illness. Preferably the stages include an acute stage (on admission), early convalescence (seven days after admission), late convalescence (six weeks after discharge) and after full recovery (3 months and twelve months after discharge).

Preferably the peripheral blood is heparinised or treated with EDTA and the PBMCs may be isolated therefrom by centrifugation.

Preferably the PBMCs are initially cultured in medium containing human serum. Preferably the PBMCS are cultured with the neisserial proteins and Interleukin 2 (IL-2) for a predetermined period. Preferably the predetermined period is 3–10 days and may be 5 days.

Preferably IL-2 stimulates the proliferation of the activated T-cell lines and clones. Preferably the T-cell lines and clones are maintained by weekly stimulation. The stimulation may be provided by proteins in the presence of IL-2 and feeder cells. Preferably the feeder cells are antigen presenting feeder cells and may be autologous Epstein-Barr virus transformed B-lymphocytes (EBVB).

The specificity of the T-cell lines and clones to neisserial proteins is preferably tested prior to storing for example in liquid nitrogen. Preferably the specificity is tested by measurement of tritiated thymidine incorporation in response to stimulation with neisserial proteins compared to irrelevant antigens. Such an irrelevant antigen may be tetanus toxoid. The phenotypes of the T-cell lines and clones are preferably also assessed using flow cytometry and specific monoclonal antibodies. The antibodies are preferably $CD4^{+,}$ $^{CD}8^-$ and $\alpha/\beta$- and $\gamma/\delta$- T-cell receptor (TCR) specific monoclonal antibodies.

In a second aspect the present invention provides a method of detecting $CD4^+$ T-cell stimulating proteins, the method comprising fractionating neisserial proteins and testing the ability of said proteins to stimulate proliferation of T-cell lines and clones.

Preferably the T-cell lines and clones are *Neisseria* specific T-cell lines and clones generated according to the method of the first aspect of the invention, as set out above.

The proteins may be fractionated by SDS-PAGE. The fractions are preferably tested for their ability to stimulate the individual T-cell lines and clones. Preferably fractions containing T-cell stimulants are further characterised by SDS-PAGE Polyclonal antibodies may be raised to the T-cell stimulating fraction proteins. The antibodies are preferably used to screen a genomic meningococcal and/or gonococcal expression library. Preferably the expression library is a λZapII library. Isolated neisserial polypeptides which react with the antibodies and their respective DNA fragments are preferably further characterised and sequenced.

In a third aspect, the present invention provides a method of detecting CD4+ T-cell stimulating recombinant proteins, the method comprising screening a genomic meningococcal or gonococcal expression library for recombinant proteins which stimulate T-cell lines and clones.

Preferably the T-cell lines and clones are meningococcal and/or gonococcal specific T-cell lines and clones generated according to the method of the first aspect of the invention, as set out above.

Preferably the genomic meningococcal or gonococcal expression library is a λZapII phage library expressing genomic DNA extracted from a strain of *Neisseria meningitidis* or a strain of *Neisseria gonorrhoea*. Preferably a representative pool of recombinant pBluescript SKII plasmid are excised from the phage library and transformed into *E. coli* strain XL1-Blue. Preferably the plasmids are excised into XL1-Blue using a helper phage.

The transformed *E. coli* are preferably cultured in a medium which may contain ampicillin. Meningococcal or gonococcal protein expression is preferably induced by isopropyl-b-D-thio-galactoside.

Preferably the bacteria are heat-killed and sonicated before adding to antigen presenting cells. The expressed proteins are preferably tested for their ability to stimulate the individual T-cell lines and clones. Preferably CD4+ T-cell stimulating bacterial cultures are identified and subcultured. The subcultures are preferably rescreened for T-cell stimulation.

Preferably the CD4+ T-cell stimulants are identified by sequencing and may be further characterised.

Alternatively the genomic meningococcal or gonococcal expression library is a λZapII phage library expressing genomic DNA extracted from a meningococcal or gonococcal genomic lambda phage display library.

In a fourth aspect the present invention provides a method of detecting CD4+ T-cell stimulating peptides, the method comprising screening meningococcal or gonococcal genomic phage display libraries (PDLs) to identify peptides which stimulate T-cell lines and clones.

Preferably the T-cell lines and clones are meningococcal and/or gonococcal specific T-cell lines and clones generated according to the method of the first aspect of the invention, as set out above.

Preferably the genomic phage display library (PDL) is generated by fragmenting bacterial DNA, cloning and packaging into bacteriophage vectors. Preferably two vectors are used. The first vector preferably displays peptides up to 1200 amino acids which are expressed at low copy numbers. The second vector preferably displays up to 415 copies of a peptide up to 50 amino acids in size.

Preferably the PDLs are amplified in respective *E. coli* hosts. The cells are preferably heat killed before testing for the ability of the peptides to stimulate the T-cell lines and clones.

Preferably CD4+ T-cell stimulating PDL cultures are identified and subcultured. The subcultures are preferably rescreened for T-cell stimulation.

Preferably the CD4+ T-cell stimulants are identified by sequencing and may be further characterised.

In a fifth aspect the present invention provides a method of detecting CD4+ T-cell stimulating recombinant proteins, using a meningococcal or gonococcal genomic lambda phage display library in accordance with the third aspect of the invention, as set out above.

The meningococcal or gonococcal genomic lambda phage display library is preferably constructed by cloning randomly amplified PCR products using two random primers, each tagged at 5' end to restriction sites, inserting same into a pre-digested vector, and plating by infecting *E. coli*.

Preferably the vector is a lambda phage and is preferably λpRH825 vector. The amplified and digested DNA fragments are preferably packaged into the lambda phage using a lambda phage packaging kit. Preferably the restriction sites are SpeI or NotI.

Preferably the DNA inserts in the plaques formed are sequenced, thereby confirming that the plaques contain DNA fragments of meningococcal or gonococcal origin.

In a sixth aspect the present invention provides the use of a polypeptide in the manufacture of a vaccine against neisserial disease, the peptide comprising an amino acid sequence as shown in SEQIDNO1 and SEQIDNO2 or an active derivative thereof.

Preferably the polypeptide is a CD4+ T-cell stimulant.

In a seventh aspect of the present invention there is provided a DNA construct for use in the manufacture of a medicament for the treatment of neisserial disease, the construct comprising a sequence as shown in SEQIDNO3 or an active derivative thereof.

In an eighth aspect the present invention provides the use of a polypeptide in the manufacture of a vaccine against neisserial disease, the peptide comprising an amino acid sequence as shown in SEQIDNO3 and SEQIDNO4 or an active derivative thereof.

Preferably the polypeptide is a CD4+ T-cell stimulant.

According to a further aspect, there is provided a DNA construct for use in the manufacture of a medicament for the treatment of neisserial disease, the construct comprising a sequence as shown in SEQIDNO1, or an active derivative thereof.

In a still further aspect the invention provides a composition for use as a vaccine against neisserial disease, the composition comprising two peptides with the amino acid sequences as shown in SEQIDNO1 and SEQIDNO2, and SEQIDNO3 and SEQIDNO4 or active derivatives thereof.

In a further aspect of the present invention there is provided a nucleotide sequence comprising a base sequence as shown in SEQIDNO1, or an active derivative thereof, the sequence coding for a polypeptide having an amino acid sequence as shown in SEQIDNO1 and SEQIDNO2, or an active derivative thereof.

In a still further aspect of the present invention there is provided a nucleotide sequence comprising a base sequence as shown in SEQIDNO3, or an active derivative thereof, the sequence coding for a polypeptide having an amino acid sequence as shown in SEQIDNO3 and SEQIDNO4, or an active derivative thereof.

The invention also provides a vaccine against neisserial disease, the vaccine comprising polypeptide with some or all of the amino acid sequence as shown in SEQIDNO2, or an active derivative thereof.

The invention provides a further vaccine against neisserial disease, the vaccine comprising polypeptide with some or all of the amino acid sequence as shown in SEQIDNO4, or an active derivative thereof.

According to a further aspect of the present invention there is provided a method of treatment of neisserial disease, the method comprising inducing T-cell proliferation with polypeptide comprising one or both of the or some of the amino acid sequences shown in SEQIDNO2 and SEQIDNO4, or active derivative(s) thereof.

The invention also provides a purified and isolated DNA composition comprising the sequences of SEQIDNO1 or SEQIDNO3, or an active derivative thereof.

Embodiments of the invention will now be described by way of example only and with reference to the accompanying drawings and sequences, in which:

DETAILED DISCLOSURE

SEQIDNO1 shows the nucleotide base sequence and the corresponding amino acid sequence of a gene and a polypeptide (TspA) encoded thereby, according to one aspect of the present invention;

SEQIDNO2 shows the polypeptide sequence of SEQIDNO1;

SEQIDNO3 shows the nucleotide base sequence and the corresponding amino acid sequence of a gene and a polypeptide (TspB) encoded thereby, according to another aspect of the present invention; and SEQIDNO4 shows the polypeptide sequence of SEQIDNO3.

In order to identify meningococcal CD4+ T-cell-stimulating peptides we adopted a number of different programmes all of which involve screening meningococcal peptide antigens, using meningococcal-specific CD4+ T-cell lines and clones. These lines and clones have been generated over the past five years or so, from the peripheral blood of normal donors and patients recovering from invasive meningococcal disease. In-vitro studies have been carried out with primed human T-cells obtained from naturally infected patients, with fresh peripheral blood samples obtained from patients at different stages of illness, namely the acute stage (on admission), early convalescence (seven days after admission), late convalescence (six weeks after discharge) and after full recovery (3 months and twelve months after discharge). T-cell lines and clones, specific to meningococcal proteins have been generated from the peripheral blood of patients recovering from meningococcal disease and healthy donors. The healthy donors were identified among twenty five volunteers by testing their peripheral blood mononuclear cells (PBMC) proliferation in response to meningococcal proteins.

Figure 1:
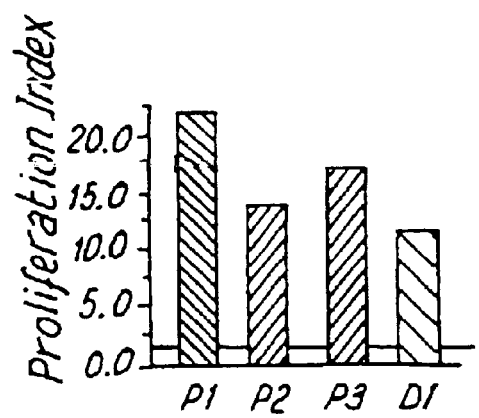
FIG. 1 is a graph illustrating the proliferation responses of peripheral blood mononuclear cells (PBMCs) of three patients and a healthy donor to meningococcal proteins.

Lymphocyte Proliferation Assays:

Briefly, PBMCs were isolated from heparinised blood samples by centrifugation over an aseptically filtered solution for human mononuclear cell separation. One such solution is sold under the tradename Histopaque® and is commercially available from Sigma-Aldrich Corp., having place of business in St. Louis. Mo. USA. The PBMCs were washed and cultured in 96-well tissue culture plates at $2 \times 10^5$ cells/well in RPMI medium containing 10% human AB serum (RPMI-AB). Meningococcal proteins (from strain SD, B:15:P1,16) were prepared by growing the organism under iron restriction, to induce the expression of iron-regulated proteins which are also expressed in vivo. Such as described by Ala'Aldeen. D. et al. 1994. "Immune response in man and animals to meningococcal transferring-binding proteins: implications for vaccine design", Infect. Immun. 62:2894–2900, (hereinafter Ala'Aldeen, 1994). The meningococcal proteins (SD-), antigens from Candida albicans (a recall antigen) or phytohaemaglutinin (PHA, positive control) were added to quadruplicate wells. RPMI-AB alone (with no antigen) was added to quadruplicate wells to serve as the background. After five days all cultures were pulsed with 1 $\mu$Ci of tritrated thymidine and incorporation of thymidine was determined after another eighteen house. A positive response was defined as PBMC proliferation index of at least 2 (See FIG. 1).

Continuous T-cell lines were established by culturing PBMCs with the meningococcal proteins and Interleukin 2 (IL-2) for five days, and activated T-cell blasts were stimulated to proliferate by a further nine days culture with IL-2 only. The lines were then maintained by weekly stimulation with proteins in the presence of feeder cells and IL-2. Autologous Epstein-Barr virus transformed B-lymphocytes (EBVB) were used as antigen-presenting feeder cells following irradiation (6000R).

T-cell clones are defined here as the population of cells which originate from a single T-cell. Single T-cell receptors (TCRs) cane engage with an extraordinary small number of peptide-HLA complexes (<10/cell) as shown in "Serial triggering of many T cell receptors by a few peptide-MHC complexes." Valitute et al. Nature 1995: 375: 148–151, hereby incorporated by reference, therefore T-cell clones will provide a highly sensitive system by which it will be possible to detect the presence of peptide antigens within mixtures of proteins. T-cell lines, specific to meningococcal antigens, were seeded at 0.3 cell/well in 96-well tissue culture plates in the presence of irradiated (non-proliferating) autologous EBVB feeder cells, plus low doses of IL-2 as reported in "Selection of T cell epitopes and vaccine engineering." Sinigaglia et al., Methods in Enzymology 1991: 203: 370–386, hereby incorporated by reference. Cell growth was detected microscopically after one-two weeks and growing cells expanded further by stimulation with meningococcal proteins. All T-cell lines and clones were assessed for the phenotype (and ascertained to be CD4+ T-cells), using flow cytometry and CD4, CD8 and $\alpha/\beta^-$ and $\gamma/\delta^-$ TCR-specific monoclonal antibodies. Their specificity to meningococcal proteins was tested by measurement of tritiated thymidine incorporation in response to stimulation with meningococcal proteins compared to irrelevant antigens e.g. tetanus toxoid. Large numbers of T-cell lines, oligoclones and clones from patients and normal donors have been identified and stored in liquid nitrogen until further use.

T-cell Responses to Fractionated Meningococcal Proteins

Figure 2:
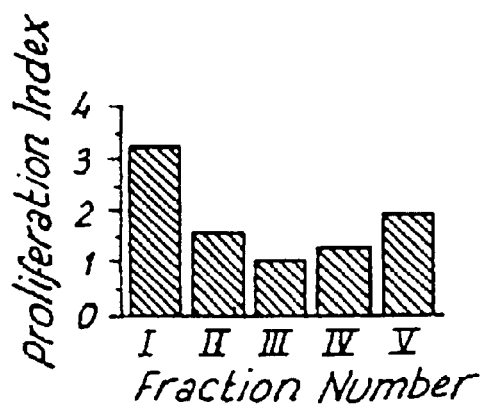
FIG. 2 is a graph illustrating the proliferation indices of a T-cell line with fraction (SI-V) of meningococcal proteins separated by SDS PAGE.

Meningococcal proteins were fractionated according to their molecular weights by SDS-polyacrylamide gel electrophoresis (SDS-PAGE). Two methods were used to prepare the separated proteins for addition to the T-cell cultures:

a) Fractionated proteins were transferred onto nitrocellulose membranes which were transversely divided into five equal sections labelled SI-V, containing proteins of approximate molecular weight range>130 kDa, 70–130 kDa, 50–70 kDa, 34–50 kDa and <34 kDa, respectively. Membranes were then solubilised with dimethyl sulphoxide and tested for their ability to stimulate T-cells using the established meningococcal specific T-cell lines. Using one of the cell lines, section SI (which contained proteins>130 kDa) caused greater T-cell proliferation than any of the other sections (FIG. 2). T-cell lines fed with either EBV-B-cells or fresh autologous PBMCs consistently gave similar results.

b) In the second method, SDS-gels containing the fractionated proteins were cut into transverse sections corresponding to the five fractions obtained by the nitrocellulose membrane method. The proteins were then directly eluted from the gel sections and purified by precipitation with organic solvents. This enabled measurement of the protein concentrations in each fraction and confirmation that differences in protein concentration were not responsible for the differences observed in FIG. 2. Equivalent concentrations of purified proteins were used in lymphocyte proliferation assays. The results were consistent with those of the nitrocellulose membrane blot method (not shown).

Figure 3:
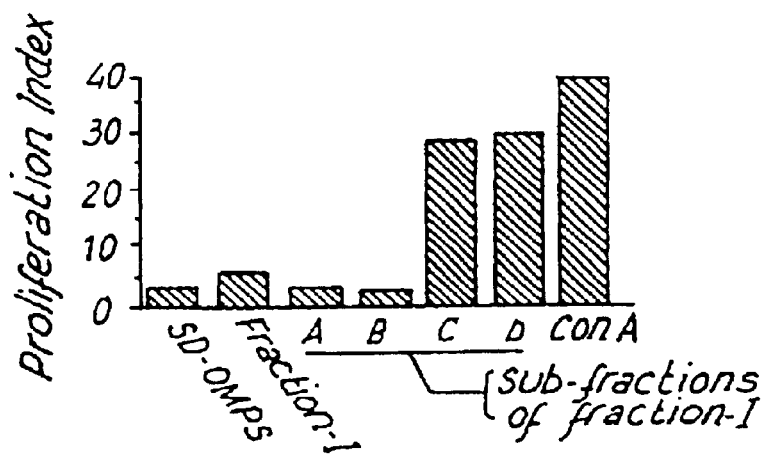
FIG. 3 is a graph illustrating the proliferation indices of a T-cell line to subfractions A, B, C and D of section SI in FIG. 2, and also the proliferation index of concanavalin A (Con A) and whole cell lysate of iron-depleted meningococci (SD-).

Section S1 consists of more than 12 proteins as seen on silver stained gels, ranging from 130–599 kDa (not shown). Therefore, it was subdivided into four fractions, FIA-D, and their proteins were eluted from gels as described above. The eluted proteins were tested for their ability to stimulate T-cell proliferation. As shown in FIG. 3, using T-cell line of a patient, fractions FIC and D induced extremely high T-cell proliferation indices (c 30), higher than fractions FIA and FIB, the whole of S1 or the total SD-protein preparation. Another T-cell line showed the highest T-cell stimulation indices with fraction FIB and FIC, followed by FID, possibly reflecting the HLA specific response.

FIC was chosen for further characterization and silver staining of SDS-gels showed that it contains four distinct protein bands (not shown). Rabbit polyclonal antibodies were raised to eluted FIC proteins and used to screen an already established genomic expression (λ Zap II) library. Several reactive meningococcal polypeptides and their respective DNA fragments were isolated. Two of the most promising ones (TspA and TspB) were further studied. The DNA fragments were sequenced and with help from the Sanger-released genomic sequences which were produced by the *Neisseria Meningitidis* Sequencing Group at the Sanger Centre. The genes encoding these two proteins were then constructed (see SEQIDNO1–4) and cloned into high expression vectors.

TspA, the abbreviation for T-cell stimulating protein A identified and characterised as part of the present invention has a genetic sequence substantially as shown in SEQIDNO1 and a corresponding polypeptide sequence as shown in SEQIDNO2.

TspA can be used to create a vaccine against pathogenic *neisseria*, and in particular *Neisseria meningitidis*, as well as *Neisseria gonorrhoea*. Determination of the sequence enables the generation of antibodies using general polyclonal and/or monoclonal techniques.

Similarly with TspB (T-cell stimulating protein B), vaccine or a component for a combination vaccine are created using polyclonal and/or monoclonal techniques.

It is envisaged that an effective vaccine will-be a combination vaccine comprising a plurality of different antigens including TspA and TspB.

The exact sequences can vary among different isolates of meningococci due to the nature of the organism and its ability to mutate any gene any time. This is a universal problem inherent with any gene of these *Neisseria* organisms. Equivalent genes with homologous sequences exist in *Neisseria gonorrhoea*, as detected on the recently released gonococcal genomic sequence data obtained on the Internet from Oklahoma University, U.S.A.

Western blot experiments on TspA and TspB, using human convalescent sera, confirmed that both proteins are expressed in-vivo and stimulate B-cells following natural infection. The cloned proteins also induced strong $CD4^+$ T-cell stimulatory effect in our T-cell proliferation assays. These suggested very clearly that they are promising vaccine candidates, and vaccines comprising one or both of these either together or with other proteins are therefore provided as part of this invention.

Finally, fractions FIB and FID, and Section SII and SV which produced net-positive T-cell stimulatory effects may consists of many T-cell stimulatory antigens (FIGS. 1 and 3).

Detection of T-cell Antigens by Phage-expression Cloning

The present invention also provides a robust screening system for the identification of $CD4^+$ T-cell stimulating recombinant proteins, using an expression cloning protocol, which involves screening genomic meningococcal expression libraries.

1. λZapII Expression Library

This method had been successfully applied in other organisms to identify helper T-cell epitopes as disclosed in "Identification of a $CD4^+$ T cell stimulating antigen of a pathogenic bacteria by expression cloning." Sanderson et al., J Exp Med 1995; 182: 1751–1757 and in "Expression cloning of a Protective *leishmania* antigen." Mougneau et al., Science 1995; 268: 563–566 each of which are hereby incorporated by reference in their entirety. Briefly, we used an existing λZapII phage library expressing genomic DNA extracted from strain SD *N. meningitidis* and is disclosed in "*Neisseria meningitides* transferring-binding protein 1 expressed in *Escherichia coli* is surface exposed and binds human transferring." Palmer et al., FEMS Microbiol Lett 1993: 110: 139–146, hereby incorporated by reference. The library contains $2\times10^5$ recombinants with an average size of insert of 2.3 kb (range up to 10 kb). A representative pool of recombinant pBluescript SKII plasmid were excised (in vivo) from the phage library and transformed into *E. coli* strain XL 1-Blue, using ExAssist helper phage (Stratgene) as described in "Cloning sequencing, characterisation and implications on vaccine design of the novel dihydrolipoyl acetyltransferase of *neisseria meningitidis*." Ala'Aldeen et al., J Med Microbiol 1996; 45: 419–432 and Palmer, 1993 supra.

Transformed *E coli* with the pBluescript plasmid carrying meningococcal genes were diluted in selective culture media (containing ampicillin) and put in 96-well microtitre plates at 20–30 transformants/wells. The plates were incubated overnight at 37° C. with shaking and replicate cultures were made by splitting the overnight cultures, and the original master plates stored at 4° C. The splits were grown in epindorfs for 2–3 hours in fresh medium to $OD_{600}$=0.3, then incubated for an additional 2 h with 1 mM isopropyl-b-D thio galactoside (IPTG) to induce meningococcal protein expression. Bacteria were heat-killed, sonicated and added to the antigen presenting cells, and tested for their ability to stimulate individual T-cell lines and clones. Negative controls were sonicates of the same E. coli strain transformed with pBluescript SKII with no meningococcal DNA insert. Strong T-cell stimulating wells were identified and their corresponding reference wells diluted and subcultured. Up to 100 single colonies (representing single organisms with single plasmids) were isolated and re-screened for T-cell stimulation. Only potent T-cell stimulants were saved and further pursued. This aspect of the present invention proved highly rewarding, and so far two, previously unknown, potent T-cell stimulating meningococcal polypeptides have been identified and further characterised.

2. T-cell Antigen Detection Using Phage Display Libraries (PDL)

Displaying foreign peptides on the surface of bacteriophages is a relatively new but well-established technology. This is different from the normal phage libraries which carry the cloned genes and express and release the proteins inside a host bacterium and not on their own outer coat. In phage display libraries, displayed peptides are encoded as DNA inserts-in the structural gene for one of the viral coat proteins and will then appear on the surface of the phage capsid. There are several phage display systems available, each with specific advantages. For example, some are filamentous and others are lytic, some are used as random display libraries (non-specific) which may be used to detect mimotopes, and others are more specific genomic libraries. It is important to note that most phage display libraries have been probed with antibodies in search of specific peptides. A highly novel approach comprising a further aspect of the present invention was developed involving the use of T-cell lines/clones to screen two different meningococcal genomic PDLs to identify good T-cell stimulating peptides.

a) T7Select1 and T7Select415 PDL

One of the novel lytic bacteriophages is Novagen's T7Select Phage Display System which is easy to use and has the capacity to display peptides up to 1200 amino acids, equivalent to 3.6 kb, with protein molecular weight over 100 kDa. Such high molecular weight proteins are usually expressed at low copy numbers by T7Select1. Phage T7Select415, however, is capable of displaying up to 415 copies of a peptide up to 50 amino acids in size. Phage assembly occurs in the E. coli cytoplasm and mature phages are release by cell lysis. The latter process occurs within a few hours of infection, which makes the system very rapid. To create a genomic display library, meningococcal DNA will be fragmented to appropriate sizes and cloned and packaged into both T7Select1 and T7Select415 vectors as described in the Novagen's T7Select System manual. This dual approach allows for the screening for both large and small polypeptides.

A representative population of these PDLs expressing meningococcal proteins are diluted and distributed as oligoclones into 96-well microtitre plates. To each well, appropriate E. coli host strains (BL,21 for T7Select415 and BLT5403 for T7Select1) will be added to amplify the diluted phage population in these wells. The plates will be split into identical duplicates, one of which a will be stored as the reference, and the other heat-killed and tested for the ability to stimulate the T-cell lines/clones as described above for the λZAPII library.

b) λpRH825 Random Meningococcal Epitope Display Library

Another method according to the present invention involves the use of proteins and small peptides on a modified lambda capsid protein D. This protein, which is of 11 kDa with 405 copies expressed as trimers on the phage head is capable of an efficient display of foreign peptides that are fused to its amino- or carboxy-termini and are disclosed in "Display of peptides and proteins on the surface of bacteriophage lambda." Sternberg et al. Proc Natl Acad Sci USA, 1995: 92: 1609–1613 and "Surface display of proteins on bacteriophage lambda heads." Mikawa et al. J Mol Biol 1996: 262: 21–30, both of which are hereby incorporated by reference. This system was successfully used to display a Hepatitis C genomic cDNA library and, more recently, to generate a randomly amplified genomic PDL of known organisms. This involves generating randomly amplified DNA fragments of a known DNA template, using short (random) oligonucleotide primers in polymerase chain reaction (PCR). We have recently constructed a meningococcal genomic lambda phage display library by cloning randomly amplified PCR products in λpRH825 vector, using two random primers, each tagged at 5' end to SpeI or NotI restriction sites to facilitate insertion into the predigested vector. Packaging amplified and digested DNA fragments into lambda phage was performed using a lambda packaging kit (Pharmacia Biotech) and plated by infection of the E. coli strain BB4. This yielded $5 \times 10^7$ plaques, of which a sample of 100 pfu were randomly chosen, and their DNA inserts sequenced. Sequence alignment of the obtained sequence data with those available for N. Meningitidis and/or N. Gonorrhoea, confirmed that all the chosen plaques contained DNA fragments of meningococcal origin. The fragment sizes ranged from 100–200 bp, representing deduced peptides of up to 60 amino acids long. This PDL was prepared and established in IRBM for use in the identification of CD4+ T-cell stimulating recombinant peptides, using the same cloning technique described for the λZapII phage system.

Several selection criteria have been adopted to focus the search for relevant, potent promiscuous-T-cell epitopes.

Initially, only candidate peptides, which are likely to contain multiple T-cell epitopes that are immunogenic for CD4+ Th-cells (not CD8+ T-cells) and presented on MHC class II (HLA-DR, DQ or DP in humans) were studied. Only T-helper (Th) antigens, that bind to a number of widely ranging HLA-types, were selected. It will be determined whether each patient's CD4+ Th-response to a candidate meningococcal peptide is due to an established memory Th population (CD45RO+) or to activation of naive T-cells (CD45RA+). Peptide candidates which activate either the Th2 subset of CD4+ T-cell or the Th1 subset are selected. The therapeutic efficacy of both Th1 and Th2-inducing candidate peptides will be evaluated. T-cell clones specific for candidate antigens will be amplified and used to identify the individual T-cell epitopes.

In order to identify and then characterise core epitopes of each candidate peptide, progressively smaller fragments of the DNA will be cloned, expressed and further examined for T-cell stimulation. To define epitopes more accurately, short overlapping peptides representing the defined T-cell stimulating subunits are synthesised and re-examined. Then N- and C-terminal truncated analogs of the most immunogenic peptide fragment are synthesised and tested likewise. Finally, alanine scanning mutational analysis will be employed to identify critical amino acid positions responsible for both TCR contact and HLA-class II contact. Here, a series of peptide analogs of the core epitope identified in after N- and C-terminal truncation are synthesised, each with single alanine substituted at successive amino acid positions, and effects on T-cell immunogenicity and on HLA-binding are assessed. The isotype of class II HLA molecule restriction specificity will be identified for each T-cell clone by antibody blocking experiments.

As a part of the characterisation of the identified proteins, the diversity of these proteins among various strains of meningococci is studied. A large collection of clinical isolates of meningococci have been prepared, the proteins of these strains when purified (from the gels or clones), and tested for T-cell stimulatory capacity and characterised in a way similar to that used for strain SD will provide further vaccine candidates. Proteins that are expressed in all or more of these stains will be focused on.

Identification of HLA Restriction

To determine whether different HLA class II molecules present different parts of individual proteins, one of two methods are used. The protein sub-fragments and their overlapping peptides described above will be tested for their capacity to stimulate T-cell clones generated from different individuals (volunteers or patients). Alternatively, lymphocyte donors will be HLA typed, and the association of responsiveness to particular proteins (or epitopes) and certain alleles of HLA-DR, -DQ or -DP determined.

A central aim is to identify T-cell immunogens of *N. meningitidis* which will stimulate T-cell help for the production of protective anti-meningococcal antibodies. Having identified dominant T-cell antigens amongst the proteins, their ability to stimulate T-cell help for antibody production is invesitigated in vivo in animals and in an in vitro immunisation system which has been established and optimised in our laboratories and is disclosed in "Simulation of human B cells specific for *Candida albicans* for monoclonal antibody production." Davenport et al. FEMS Microbiol Immunol 1992: 89: 335–344. Protein fragments Protein fragments of peptides that stimulate T-cells from individuals covering a range of HLA types are studied for the presence of B-cell epitopes. If the protein contains B-cell epitopes then anitbodies from individuals naturally immune to meningococcal disease should recognise these proteins in immunoblots or ELISA. If no B-cell epitopes are recognised then the identified T-cell epitopes will be conjugated to previously characterised B-cell immunogens such as meningococcal capsular polysaccharides, the class (1, 2/3) proteins, the transferrin binding protein . . . etc.

Whilst endeavouring in the foregoing specification to draw attention to the features of the invention believed to be of particular importance it should be understood that the Applicant claims protection in respect of any patentable feature hereinbefore referred to and/or shown in the drawings whether or not particular emphasis has been placed thereon.

What is claimed is:

1. An isolated T cell-stimulating meningococcal polypeptide comprising the amino acid sequence of SEQ ID NO: 2.

2. A composition comprising the polypeptide of claim 1.

* * * * *

SEQUENCE LISTING

```
<160> NUMBER OF SEQ ID NOS: 4

<210> SEQ ID NO 1
<211> LENGTH: 2761
<212> TYPE: DNA
<213> ORGANISM: Neisseria meningitidis
<220> FEATURE:
<221> NAME/KEY: CDS
<222> LOCATION: (119)..(2761)
<223> OTHER INFORMATION:

<400> SEQUENCE: 1
gattgatgca aatatgcaca gatgtttttg aaaaaagatg gagatatgtc ataatttgta      60
aaaacggcga atgattgccg tttaaaatgt ggcggcggtc ggtacattca catattaa       118 atg ccc gcc ggc cga ctg ccc cgc cga tgc ccg atg atg acg aaa ttt       166
Met Pro Ala Gly Arg Leu Pro Arg Arg Cys Pro Met Met Thr Lys Phe
1               5                   10                  15 aca gac tgt acg cgg tca aac cgt att cag ccg cca acc cac agg gga       214
Thr Asp Cys Thr Arg Ser Asn Arg Ile Gln Pro Pro Thr His Arg Gly
            20                  25                  30 tac atc ttg aaa aac aac aga caa atc aaa ctg att gcc gcc tcc gtc       262
Tyr Ile Leu Lys Asn Asn Arg Gln Ile Lys Leu Ile Ala Ala Ser Val
        35                  40                  45 gca gtt gcc gca tcc ttt cag gca cat gct gga ctg ggc gga ctg aat       310
Ala Val Ala Ala Ser Phe Gln Ala His Ala Gly Leu Gly Gly Leu Asn
    50                  55                  60 atc cag tcc aac ctt gac gaa ccc ttt tcc ggc agc att acc gta acc       358
Ile Gln Ser Asn Leu Asp Glu Pro Phe Ser Gly Ser Ile Thr Val Thr
65                  70                  75                  80 ggc gaa gaa gcc aaa gcc ctg cta ggc ggc ggc agc gtt acc gtt tcc       406
Gly Glu Glu Ala Lys Ala Leu Leu Gly Gly Gly Ser Val Thr Val Ser
                85                  90                  95
```

-continued

| | |
|---|---|
| gaa aaa ggc ctg acc gcc aaa gtc cac aag ttg ggc gac aaa gcc gtc<br>Glu Lys Gly Leu Thr Ala Lys Val His Lys Leu Gly Asp Lys Ala Val<br>100 105 110 | 454 |
| att gcc gtt tct tcc gaa cag gca gtc cgc gat ccc gtc ctg gta ttc<br>Ile Ala Val Ser Ser Glu Gln Ala Val Arg Asp Pro Val Leu Val Phe<br>115 120 125 | 502 |
| cgc atc ggc gca ggc gca cag gta cgc gaa tac acc gcc atc ctc gat<br>Arg Ile Gly Ala Gly Ala Gln Val Arg Glu Tyr Thr Ala Ile Leu Asp<br>130 135 140 | 550 |
| cct gtc ggc tac tcg ccc aaa acc aaa tct gca ctt tca gac ggc aag<br>Pro Val Gly Tyr Ser Pro Lys Thr Lys Ser Ala Leu Ser Asp Gly Lys<br>145 150 155 160 | 598 |
| aca cac cgc aaa acc gct ccg aca gca gag tcc caa gaa aat caa aac<br>Thr His Arg Lys Thr Ala Pro Thr Ala Glu Ser Gln Glu Asn Gln Asn<br>165 170 175 | 646 |
| gcc aaa gcc ctc cgc aaa acc gat aaa aaa gac agc gcg aac gca gcc<br>Ala Lys Ala Leu Arg Lys Thr Asp Lys Lys Asp Ser Ala Asn Ala Ala<br>180 185 190 | 694 |
| gtc aaa ccg gcg tac aac ggc aaa acc cat acc gtc cgc aaa ggc gaa<br>Val Lys Pro Ala Tyr Asn Gly Lys Thr His Thr Val Arg Lys Gly Glu<br>195 200 205 | 742 |
| acg gtc aaa cag att gcc gcc gcc atc cgc ccg aaa cac ctg acg ctc<br>Thr Val Lys Gln Ile Ala Ala Ala Ile Arg Pro Lys His Leu Thr Leu<br>210 215 220 | 790 |
| gaa cag gtt gcc gat gcg ctg ctg aag gca aac cca aat gtt tcc gca<br>Glu Gln Val Ala Asp Ala Leu Leu Lys Ala Asn Pro Asn Val Ser Ala<br>225 230 235 240 | 838 |
| cac ggc aga ctg cgt gcg ggc agc gtg ctt cac att ccg aat ctg aac<br>His Gly Arg Leu Arg Ala Gly Ser Val Leu His Ile Pro Asn Leu Asn<br>245 250 255 | 886 |
| agg atc aaa gcg gaa caa ccc aaa ccg caa acg gcg aaa ccc aaa gcc<br>Arg Ile Lys Ala Glu Gln Pro Lys Pro Gln Thr Ala Lys Pro Lys Ala<br>260 265 270 | 934 |
| gaa acc gca tcc atg ccg tcc gaa ccg tcc aaa cag gca acg gta gag<br>Glu Thr Ala Ser Met Pro Ser Glu Pro Ser Lys Gln Ala Thr Val Glu<br>275 280 285 | 982 |
| aaa ccg gtt gaa aaa cct gaa gca aaa gtt gcc gcg ccc gaa gca aaa<br>Lys Pro Val Glu Lys Pro Glu Ala Lys Val Ala Ala Pro Glu Ala Lys<br>290 295 300 | 1030 |
| gcg gaa aaa ccg gcc gtt cga ccc gaa cct gta ccc gct gca aat act<br>Ala Glu Lys Pro Ala Val Arg Pro Glu Pro Val Pro Ala Ala Asn Thr<br>305 310 315 320 | 1078 |
| gcc gca tcg gaa acc gct gcc gaa tcc gcc ccc caa gaa gcc gcc gct<br>Ala Ala Ser Glu Thr Ala Ala Glu Ser Ala Pro Gln Glu Ala Ala Ala<br>325 330 335 | 1126 |
| tct gcc atc gac acg ccg acc gac gaa acc ggt aac gcc gtt tcc gaa<br>Ser Ala Ile Asp Thr Pro Thr Asp Glu Thr Gly Asn Ala Val Ser Glu<br>340 345 350 | 1174 |
| cct gtc gaa cag gtt tct gcc gaa gaa gaa acc gaa agc gga ctg ttc<br>Pro Val Glu Gln Val Ser Ala Glu Glu Glu Thr Glu Ser Gly Leu Phe<br>355 360 365 | 1222 |
| ggc ggt tcg tac acc ttg ctg ctt gcc ggc gga ggc gcg gca ttg atc<br>Gly Gly Ser Tyr Thr Leu Leu Leu Ala Gly Gly Gly Ala Ala Leu Ile<br>370 375 380 | 1270 |
| gcc ctg ctg ctg ctt ttg cgc ctt gcc caa tcc aaa cgc gcg cgc cgt<br>Ala Leu Leu Leu Leu Leu Arg Leu Ala Gln Ser Lys Arg Ala Arg Arg<br>385 390 395 400 | 1318 |
| acc gaa gaa tcc gtc cct gag gaa gag cct gac ctt gac gac gcg gca<br>Thr Glu Glu Ser Val Pro Glu Glu Glu Pro Asp Leu Asp Asp Ala Ala | 1366 |

-continued

|  |  |  |
|---|---|---|
| 405 | 410 | 415 | gac gac ggc ata gaa atc acc ttt gcc gaa gtc gaa act ccg gca acg      1414
Asp Asp Gly Ile Glu Ile Thr Phe Ala Glu Val Glu Thr Pro Ala Thr
            420                 425                 430 ccc gaa ccc gct ccg aaa aac gat gta aac gac aca ctt gcc tta gat      1462
Pro Glu Pro Ala Pro Lys Asn Asp Val Asn Asp Thr Leu Ala Leu Asp
        435                 440                 445 ggg gaa tct gaa gaa gag ttg tcg gca aaa caa acg ttc gat gtc gaa      1510
Gly Glu Ser Glu Glu Glu Leu Ser Ala Lys Gln Thr Phe Asp Val Glu
    450                 455                 460 acc gat acg cct tcc aac cgc atc gac ttg gat ttc gac agc ctg gca      1558
Thr Asp Thr Pro Ser Asn Arg Ile Asp Leu Asp Phe Asp Ser Leu Ala
465                 470                 475                 480 gcc gcg caa aac ggc att tta tcc ggc gca ctt acg cag gat gaa gaa      1606
Ala Ala Gln Asn Gly Ile Leu Ser Gly Ala Leu Thr Gln Asp Glu Glu
                485                 490                 495 acc caa aaa cgc gcg gat gcc gat tgg aac gcc atc gaa tcc aca gac      1654
Thr Gln Lys Arg Ala Asp Ala Asp Trp Asn Ala Ile Glu Ser Thr Asp
            500                 505                 510 agc gtg tac gag ccc gag acc ttc aac ccg tac aac cct gtc gaa atc      1702
Ser Val Tyr Glu Pro Glu Thr Phe Asn Pro Tyr Asn Pro Val Glu Ile
        515                 520                 525 gtc atc gac acg ccc gaa ccg gaa tct gtc gcc caa act gcc gaa aac      1750
Val Ile Asp Thr Pro Glu Pro Glu Ser Val Ala Gln Thr Ala Glu Asn
    530                 535                 540 aaa ccg gaa acc gtc gat acc gat ttc tcc gac aac ctg ccc tca aac      1798
Lys Pro Glu Thr Val Asp Thr Asp Phe Ser Asp Asn Leu Pro Ser Asn
545                 550                 555                 560 aac cat atc ggc aca gaa gaa aca gct tcc gca aaa cct gcc tca ccc      1846
Asn His Ile Gly Thr Glu Glu Thr Ala Ser Ala Lys Pro Ala Ser Pro
                565                 570                 575 tcc gga ctg gca ggc ttc ctg aag gct tcc tcg ccc gaa acc atc ttg      1894
Ser Gly Leu Ala Gly Phe Leu Lys Ala Ser Ser Pro Glu Thr Ile Leu
            580                 585                 590 gaa aaa aca gtt gcc gaa gtc caa aca ccg gaa gag ttg cac gat ttc      1942
Glu Lys Thr Val Ala Glu Val Gln Thr Pro Glu Glu Leu His Asp Phe
        595                 600                 605 ctg aaa gtg tac gaa acc gat gcc gtc gcg gaa act gcg cct gaa acg      1990
Leu Lys Val Tyr Glu Thr Asp Ala Val Ala Glu Thr Ala Pro Glu Thr
    610                 615                 620 ccc gat ttc aac gcc gcc gca gac gat ttg tcc gca ttg ctt caa cct      2038
Pro Asp Phe Asn Ala Ala Ala Asp Asp Leu Ser Ala Leu Leu Gln Pro
625                 630                 635                 640 gcc gaa gca ccg tcc gtt gag gaa aat ata acg gaa acc gtt gcc gaa      2086
Ala Glu Ala Pro Ser Val Glu Glu Asn Ile Thr Glu Thr Val Ala Glu
                645                 650                 655 aca ccc gac ttc aac gcc acc gca gac gat ttg tcc gca tta ctt caa      2134
Thr Pro Asp Phe Asn Ala Thr Ala Asp Asp Leu Ser Ala Leu Leu Gln
            660                 665                 670 cct tct gaa gta cct gcc gtt gag gaa aat gca gcg gaa atc gtt gcc      2182
Pro Ser Glu Val Pro Ala Val Glu Glu Asn Ala Ala Glu Ile Val Ala
        675                 680                 685 gat gat ttg tcc gca ctg ttg caa cct gct gaa gca ccg gct gtt gag      2230
Asp Asp Leu Ser Ala Leu Leu Gln Pro Ala Glu Ala Pro Ala Val Glu
    690                 695                 700 gaa aat gta acg gaa act gtt gcc gaa acg tcc gac ttc cac acc gcc      2278
Glu Asn Val Thr Glu Thr Val Ala Glu Thr Ser Asp Phe His Thr Ala
705                 710                 715                 720 gca gac gat ttg tcc gca ctg ttg caa cct gct gaa gta ccg gcc gtt      2326

```
Ala Asp Asp Leu Ser Ala Leu Leu Gln Pro Ala Glu Val Pro Ala Val
            725                 730                 735 gag gaa aat gta acg aaa acc gtt gcc gaa ata cct gat ttc aac gcc      2374
Glu Glu Asn Val Thr Lys Thr Val Ala Glu Ile Pro Asp Phe Asn Ala
            740                 745                 750 acc gca gac gat ttg tcc gca tta ctt caa cct tct gaa gta ccg gcc      2422
Thr Ala Asp Asp Leu Ser Ala Leu Leu Gln Pro Ser Glu Val Pro Ala
            755                 760                 765 gtt gag gaa aat gca gcg gaa atc act ttg gaa acg cct gat tcc aac      2470
Val Glu Glu Asn Ala Ala Glu Ile Thr Leu Glu Thr Pro Asp Ser Asn
    770                 775                 780 acc tct gag gca gac gct ttg ccc gac ttc ctg aaa gac ggc gag gag      2518
Thr Ser Glu Ala Asp Ala Leu Pro Asp Phe Leu Lys Asp Gly Glu Glu
785                 790                 795                 800 gaa acg gta gat tgg agc atc tac ctc tcg gaa gaa aat atc cca aat      2566
Glu Thr Val Asp Trp Ser Ile Tyr Leu Ser Glu Glu Asn Ile Pro Asn
                805                 810                 815 aat gca gat acc agt ttc cct tcg gaa tct gta ggt tct gac gcg cct      2614
Asn Ala Asp Thr Ser Phe Pro Ser Glu Ser Val Gly Ser Asp Ala Pro
            820                 825                 830 tcc gaa gcg aaa tac gac ctt gcc gaa atg tat ctc gaa atc ggc gac      2662
Ser Glu Ala Lys Tyr Asp Leu Ala Glu Met Tyr Leu Glu Ile Gly Asp
                835                 840                 845 cgc gat gcc gct gcc gag aca gtg cag aaa ttg ctg gaa gaa gcg gaa      2710
Arg Asp Ala Ala Ala Glu Thr Val Gln Lys Leu Leu Glu Glu Ala Glu
        850                 855                 860 ggc gac gta ctc aaa cgt gcc caa gca ttg gcg cag gaa ttg ggt att      2758
Gly Asp Val Leu Lys Arg Ala Gln Ala Leu Ala Gln Glu Leu Gly Ile
865                 870                 875                 880 tga                                                                  2761

<210> SEQ ID NO 2
<211> LENGTH: 880
<212> TYPE: PRT
<213> ORGANISM: Neisseria meningitidis

<400> SEQUENCE: 2

Met Pro Ala Gly Arg Leu Pro Arg Arg Cys Pro Met Met Thr Lys Phe
1               5                   10                  15

Thr Asp Cys Thr Arg Ser Asn Arg Ile Gln Pro Pro Thr His Arg Gly
            20                  25                  30

Tyr Ile Leu Lys Asn Asn Arg Gln Ile Lys Leu Ile Ala Ala Ser Val
        35                  40                  45

Ala Val Ala Ala Ser Phe Gln Ala His Ala Gly Leu Gly Gly Leu Asn
    50                  55                  60

Ile Gln Ser Asn Leu Asp Glu Pro Phe Ser Gly Ser Ile Thr Val Thr
65                  70                  75                  80

Gly Glu Glu Ala Lys Ala Leu Leu Gly Gly Ser Val Thr Val Ser
                85                  90                  95

Glu Lys Gly Leu Thr Ala Lys Val His Lys Leu Gly Asp Lys Ala Val
            100                 105                 110

Ile Ala Val Ser Ser Glu Gln Ala Val Arg Asp Pro Val Leu Val Phe
        115                 120                 125

Arg Ile Gly Ala Gly Ala Gln Val Arg Glu Tyr Thr Ala Ile Leu Asp
    130                 135                 140

Pro Val Gly Tyr Ser Pro Lys Thr Lys Ser Ala Leu Ser Asp Gly Lys
145                 150                 155                 160
```

-continued

```
Thr His Arg Lys Thr Ala Pro Thr Ala Glu Ser Gln Glu Asn Gln Asn
            165                 170                 175

Ala Lys Ala Leu Arg Lys Thr Asp Lys Lys Asp Ser Ala Asn Ala Ala
            180                 185                 190

Val Lys Pro Ala Tyr Asn Gly Lys Thr His Thr Val Arg Lys Gly Glu
            195                 200                 205

Thr Val Lys Gln Ile Ala Ala Ile Arg Pro Lys His Leu Thr Leu
            210                 215                 220

Glu Gln Val Ala Asp Ala Leu Leu Lys Ala Asn Pro Asn Val Ser Ala
225                 230                 235                 240

His Gly Arg Leu Arg Ala Gly Ser Val Leu His Ile Pro Asn Leu Asn
            245                 250                 255

Arg Ile Lys Ala Glu Gln Pro Lys Pro Gln Thr Ala Lys Pro Lys Ala
            260                 265                 270

Glu Thr Ala Ser Met Pro Ser Glu Pro Ser Lys Gln Ala Thr Val Glu
            275                 280                 285

Lys Pro Val Glu Lys Pro Glu Ala Lys Val Ala Ala Pro Glu Ala Lys
            290                 295                 300

Ala Glu Lys Pro Ala Val Arg Pro Glu Pro Val Pro Ala Ala Asn Thr
305                 310                 315                 320

Ala Ala Ser Glu Thr Ala Ala Glu Ser Ala Pro Gln Glu Ala Ala Ala
            325                 330                 335

Ser Ala Ile Asp Thr Pro Thr Asp Glu Thr Gly Asn Ala Val Ser Glu
            340                 345                 350

Pro Val Glu Gln Val Ser Ala Glu Glu Thr Glu Ser Gly Leu Phe
            355                 360                 365

Gly Gly Ser Tyr Thr Leu Leu Leu Ala Gly Gly Ala Ala Leu Ile
            370                 375                 380

Ala Leu Leu Leu Leu Leu Arg Leu Ala Gln Ser Lys Arg Ala Arg Arg
385                 390                 395                 400

Thr Glu Glu Ser Val Pro Glu Glu Pro Asp Leu Asp Asp Ala Ala
            405                 410                 415

Asp Asp Gly Ile Glu Ile Thr Phe Ala Glu Val Glu Thr Pro Ala Thr
            420                 425                 430

Pro Glu Pro Ala Pro Lys Asn Asp Val Asn Asp Thr Leu Ala Leu Asp
            435                 440                 445

Gly Glu Ser Glu Glu Glu Leu Ser Ala Lys Gln Thr Phe Asp Val Glu
            450                 455                 460

Thr Asp Thr Pro Ser Asn Arg Ile Asp Leu Asp Phe Asp Ser Leu Ala
465                 470                 475                 480

Ala Ala Gln Asn Gly Ile Leu Ser Gly Ala Leu Thr Gln Asp Glu Glu
            485                 490                 495

Thr Gln Lys Arg Ala Asp Ala Asp Trp Asn Ala Ile Glu Ser Thr Asp
            500                 505                 510

Ser Val Tyr Glu Pro Glu Thr Phe Asn Pro Tyr Asn Pro Val Glu Ile
            515                 520                 525

Val Ile Asp Thr Pro Glu Pro Glu Ser Val Ala Gln Thr Ala Glu Asn
            530                 535                 540

Lys Pro Glu Thr Val Asp Thr Asp Phe Ser Asp Asn Leu Pro Ser Asn
545                 550                 555                 560

Asn His Ile Gly Thr Glu Glu Thr Ala Ser Ala Lys Pro Ala Ser Pro
            565                 570                 575

Ser Gly Leu Ala Gly Phe Leu Lys Ala Ser Ser Pro Glu Thr Ile Leu
```

-continued

```
                    580                 585                 590
        Glu Lys Thr Val Ala Glu Val Gln Thr Pro Glu Leu His Asp Phe
            595                 600                 605

Leu Lys Val Tyr Glu Thr Asp Ala Val Ala Glu Thr Ala Pro Glu Thr
            610                 615                 620

Pro Asp Phe Asn Ala Ala Asp Asp Leu Ser Ala Leu Leu Gln Pro
        625                 630                 635                 640

Ala Glu Ala Pro Ser Val Glu Glu Asn Ile Thr Glu Thr Val Ala Glu
                            645                 650                 655

Thr Pro Asp Phe Asn Ala Thr Ala Asp Asp Leu Ser Ala Leu Leu Gln
                        660                 665                 670

Pro Ser Glu Val Pro Ala Val Glu Glu Asn Ala Ala Glu Ile Val Ala
                    675                 680                 685

Asp Asp Leu Ser Ala Leu Leu Gln Pro Ala Glu Ala Pro Ala Val Glu
            690                 695                 700

Glu Asn Val Thr Glu Thr Val Ala Glu Thr Ser Asp Phe His Thr Ala
        705                 710                 715                 720

Ala Asp Asp Leu Ser Ala Leu Leu Gln Pro Ala Glu Val Pro Ala Val
                            725                 730                 735

Glu Glu Asn Val Thr Lys Thr Val Ala Glu Ile Pro Asp Phe Asn Ala
                        740                 745                 750

Thr Ala Asp Asp Leu Ser Ala Leu Leu Gln Pro Ser Glu Val Pro Ala
                    755                 760                 765

Val Glu Glu Asn Ala Ala Glu Ile Thr Leu Glu Thr Pro Asp Ser Asn
            770                 775                 780

Thr Ser Glu Ala Asp Ala Leu Pro Asp Phe Leu Lys Asp Gly Glu Glu
        785                 790                 795                 800

Glu Thr Val Asp Trp Ser Ile Tyr Leu Ser Glu Glu Asn Ile Pro Asn
                            805                 810                 815

Asn Ala Asp Thr Ser Phe Pro Ser Glu Ser Val Gly Ser Asp Ala Pro
                        820                 825                 830

Ser Glu Ala Lys Tyr Asp Leu Ala Glu Met Tyr Leu Glu Ile Gly Asp
                    835                 840                 845

Arg Asp Ala Ala Ala Glu Thr Val Gln Lys Leu Leu Glu Glu Ala Glu
            850                 855                 860

Gly Asp Val Leu Lys Arg Ala Gln Ala Leu Ala Gln Glu Leu Gly Ile
        865                 870                 875                 880

<210> SEQ ID NO 3
<211> LENGTH: 1647
<212> TYPE: DNA
<213> ORGANISM: Neisseria meningitidis
<220> FEATURE:
<221> NAME/KEY: CDS
<222> LOCATION: (1)..(1647)
<223> OTHER INFORMATION:

<400> SEQUENCE: 3 atg aag caa aat gtt atg ttt ctt atc cta ggg cga aat ttt tta aag       48
Met Lys Gln Asn Val Met Phe Leu Ile Leu Gly Arg Asn Phe Leu Lys
1               5                   10                  15 att atc cta tgc ttt agt ttt ttt gta cct aaa ttt gca ttg gca tca       96
Ile Ile Leu Cys Phe Ser Phe Phe Val Pro Lys Phe Ala Leu Ala Ser
                20                  25                  30 gta aat gtt ccg ggt aaa ttt gat agg gtt gaa gtt tat gat gat ggc      144
Val Asn Val Pro Gly Lys Phe Asp Arg Val Glu Val Tyr Asp Asp Gly
            35                  40                  45
```

```
aga tat tta ggt att cga ggt tca gat gac aaa aga aga att tgg        192
Arg Tyr Leu Gly Ile Arg Gly Ser Asp Asp Lys Arg Arg Ile Trp
     50              55              60 aaa ggt gta ttt gat aga gaa tcg gga aga tat tta act tca gaa gct    240
Lys Gly Val Phe Asp Arg Glu Ser Gly Arg Tyr Leu Thr Ser Glu Ala
 65              70              75              80 caa gat tta aaa gtt agg cat gta tct act gga gca tca agt acg ggt    288
Gln Asp Leu Lys Val Arg His Val Ser Thr Gly Ala Ser Ser Thr Gly
                 85              90              95 aaa gtt agt tcg gtt gta tct tca tca gtt tcc cgc gcc gga gtc ttg    336
Lys Val Ser Ser Val Val Ser Ser Ser Val Ser Arg Ala Gly Val Leu
            100             105             110 gca gga gtc ggc aaa ctt gcc cgc tta ggc gcg aaa tta agc aca agg    384
Ala Gly Val Gly Lys Leu Ala Arg Leu Gly Ala Lys Leu Ser Thr Arg
        115             120             125 gca gtt cct tat gtc gga aca gcc ctt tta gcc cat gac gta tac gaa    432
Ala Val Pro Tyr Val Gly Thr Ala Leu Leu Ala His Asp Val Tyr Glu
    130             135             140 act ttc aaa gaa gac ata cag gca caa ggc tac caa tac gac ccc gaa    480
Thr Phe Lys Glu Asp Ile Gln Ala Gln Gly Tyr Gln Tyr Asp Pro Glu
145             150             155             160 acc gac aaa ttt gta aaa ggc tac gaa tat agt aat tgc ctt tgg tac    528
Thr Asp Lys Phe Val Lys Gly Tyr Glu Tyr Ser Asn Cys Leu Trp Tyr
                165             170             175 gaa gac aaa aga cgt att aat aga acc tat ggc tgc tac ggc gtt gac    576
Glu Asp Lys Arg Arg Ile Asn Arg Thr Tyr Gly Cys Tyr Gly Val Asp
            180             185             190 agt tcg att atg cgc ctt atg tcc gat gac agc aga ttc ccc gaa gtc    624
Ser Ser Ile Met Arg Leu Met Ser Asp Asp Ser Arg Phe Pro Glu Val
        195             200             205 aaa gaa ttg atg gaa agc caa atg tat agg ctg gca cgt ccg ttt tgg    672
Lys Glu Leu Met Glu Ser Gln Met Tyr Arg Leu Ala Arg Pro Phe Trp
    210             215             220 aat tgg cat aaa gaa gaa ctg aat aaa tta agt tct ttg gat tgg aat    720
Asn Trp His Lys Glu Glu Leu Asn Lys Leu Ser Ser Leu Asp Trp Asn
225             230             235             240 aat ttt gtt tta aat agt tgc aca ttt gat tgg aac ggc gga gat tgt    768
Asn Phe Val Leu Asn Ser Cys Thr Phe Asp Trp Asn Gly Gly Asp Cys
                245             250             255 gtg gtc aat aaa ggt gat gat ttc aga aat ggg gct gat ttt tcc ctt    816
Val Val Asn Lys Gly Asp Asp Phe Arg Asn Gly Ala Asp Phe Ser Leu
            260             265             270 att cgc aat tca aaa tac aaa gaa gaa atg gat gcc aaa aag ctg gaa    864
Ile Arg Asn Ser Lys Tyr Lys Glu Glu Met Asp Ala Lys Lys Leu Glu
        275             280             285 gag att tta tcg ttg aaa gtc gat gcc aat ccc gac aaa tac ata aag    912
Glu Ile Leu Ser Leu Lys Val Asp Ala Asn Pro Asp Lys Tyr Ile Lys
    290             295             300 gca acc ggt tat ccc ggt tat tcc gaa aaa gta gaa gtc gca ccc gga    960
Ala Thr Gly Tyr Pro Gly Tyr Ser Glu Lys Val Glu Val Ala Pro Gly
305             310             315             320 aca aaa gtg aat atg ggt ccc gtc acg gac agg aac ggg aat ccc gtt   1008
Thr Lys Val Asn Met Gly Pro Val Thr Asp Arg Asn Gly Asn Pro Val
                325             330             335 cag gtt gtc gca aca ttc ggc agg gat tcg caa ggc aac acc acg gtg   1056
Gln Val Val Ala Thr Phe Gly Arg Asp Ser Gln Gly Asn Thr Thr Val
            340             345             350 gat gtt caa gta atc ccg cgt ccc gac ttg acc ccc gga agc gcg gaa   1104
Asp Val Gln Val Ile Pro Arg Pro Asp Leu Thr Pro Gly Ser Ala Glu
```

-continued

```
                    355                 360                 365
gca ccg aac gca cag ccg ctg ccc gaa gta tcg ccc gcc gaa aac ccc      1152
Ala Pro Asn Ala Gln Pro Leu Pro Glu Val Ser Pro Ala Glu Asn Pro
        370                 375                 380 gca aac aac ccg aac ccc aat gag aac ccc ggc acg agc ccc aat ccc      1200
Ala Asn Asn Pro Asn Pro Asn Glu Asn Pro Gly Thr Ser Pro Asn Pro
385                 390                 395                 400 gaa ccc gac ccc gat ttg aat ccc gat gca aat ccc gat acg gac gga      1248
Glu Pro Asp Pro Asp Leu Asn Pro Asp Ala Asn Pro Asp Thr Asp Gly
                405                 410                 415 cag ccc ggc aca aga ccc gat tcc ccc gcc gtt ccg gga cgc aca aac      1296
Gln Pro Gly Thr Arg Pro Asp Ser Pro Ala Val Pro Gly Arg Thr Asn
            420                 425                 430 ggc agg gac ggc aaa gac gga aag gac ggc aaa gat ggc ggc ctt ttg      1344
Gly Arg Asp Gly Lys Asp Gly Lys Asp Gly Lys Asp Gly Gly Leu Leu
        435                 440                 445 tgc aaa ttc ttc ccc gac att ctc gct tgc gac agg ctg ccc gag tcc      1392
Cys Lys Phe Phe Pro Asp Ile Leu Ala Cys Asp Arg Leu Pro Glu Ser
    450                 455                 460 aat ccg gca gaa gat tta aat ctg ccg tct gaa acc gtc aat gta gag      1440
Asn Pro Ala Glu Asp Leu Asn Leu Pro Ser Glu Thr Val Asn Val Glu
465                 470                 475                 480 ttt cag aaa tca gga atc ttt caa gat tcc gca cag tgt ccc gca cct      1488
Phe Gln Lys Ser Gly Ile Phe Gln Asp Ser Ala Gln Cys Pro Ala Pro
                485                 490                 495 gtc act ttc aca gtg act gtg ctt gat tca agc agg cag ttc gcg ttc      1536
Val Thr Phe Thr Val Thr Val Leu Asp Ser Ser Arg Gln Phe Ala Phe
            500                 505                 510 agc ttt gag aac gca tgt acc ata gcc gaa cgg cta agg tac atg ctt      1584
Ser Phe Glu Asn Ala Cys Thr Ile Ala Glu Arg Leu Arg Tyr Met Leu
        515                 520                 525 ctc gcc ctt gct tgg gcg gtt gcc gcc ttt ttt tgt atc cgc aca gta      1632
Leu Ala Leu Ala Trp Ala Val Ala Ala Phe Phe Cys Ile Arg Thr Val
    530                 535                 540 tct cgt gaa gtc tag                                                  1647
Ser Arg Glu Val
545
```

<210> SEQ ID NO 4
<211> LENGTH: 548
<212> TYPE: PRT
<213> ORGANISM: Neisseria meningitidis

<400> SEQUENCE: 4

```
Met Lys Gln Asn Val Met Phe Leu Ile Leu Gly Arg Asn Phe Leu Lys
1               5                   10                  15

Ile Ile Leu Cys Phe Ser Phe Val Pro Lys Phe Ala Leu Ala Ser
            20                  25                  30

Val Asn Val Pro Gly Lys Phe Asp Arg Val Glu Val Tyr Asp Asp Gly
        35                  40                  45

Arg Tyr Leu Gly Ile Arg Gly Ser Asp Lys Arg Arg Ile Trp
    50                  55                  60

Lys Gly Val Phe Asp Arg Glu Ser Gly Arg Tyr Leu Thr Ser Glu Ala
65                  70                  75                  80

Gln Asp Leu Lys Val Arg His Val Ser Thr Gly Ala Ser Ser Thr Gly
                85                  90                  95

Lys Val Ser Ser Val Val Ser Ser Val Ser Arg Ala Gly Val Leu
            100                 105                 110
```

-continued

```
Ala Gly Val Gly Lys Leu Ala Arg Leu Gly Ala Lys Leu Ser Thr Arg
        115                 120                 125
Ala Val Pro Tyr Val Gly Thr Ala Leu Leu Ala His Asp Val Tyr Glu
        130                 135                 140
Thr Phe Lys Glu Asp Ile Gln Ala Gln Gly Tyr Gln Tyr Asp Pro Glu
145                 150                 155                 160
Thr Asp Lys Phe Val Lys Gly Tyr Glu Tyr Ser Asn Cys Leu Trp Tyr
                165                 170                 175
Glu Asp Lys Arg Arg Ile Asn Arg Thr Tyr Gly Cys Tyr Gly Val Asp
                180                 185                 190
Ser Ser Ile Met Arg Leu Met Ser Asp Asp Ser Arg Phe Pro Glu Val
        195                 200                 205
Lys Glu Leu Met Glu Ser Gln Met Tyr Arg Leu Ala Arg Pro Phe Trp
        210                 215                 220
Asn Trp His Lys Glu Glu Leu Asn Lys Leu Ser Ser Leu Asp Trp Asn
225                 230                 235                 240
Asn Phe Val Leu Asn Ser Cys Thr Phe Asp Trp Asn Gly Gly Asp Cys
                245                 250                 255
Val Val Asn Lys Gly Asp Asp Phe Arg Asn Gly Ala Asp Phe Ser Leu
                260                 265                 270
Ile Arg Asn Ser Lys Tyr Lys Glu Glu Met Asp Ala Lys Lys Leu Glu
        275                 280                 285
Glu Ile Leu Ser Leu Lys Val Asp Ala Asn Pro Asp Lys Tyr Ile Lys
        290                 295                 300
Ala Thr Gly Tyr Pro Gly Tyr Ser Glu Lys Val Glu Val Ala Pro Gly
305                 310                 315                 320
Thr Lys Val Asn Met Gly Pro Val Thr Asp Arg Asn Gly Asn Pro Val
                325                 330                 335
Gln Val Val Ala Thr Phe Gly Arg Asp Ser Gln Gly Asn Thr Thr Val
                340                 345                 350
Asp Val Gln Val Ile Pro Arg Pro Asp Leu Thr Pro Gly Ser Ala Glu
        355                 360                 365
Ala Pro Asn Ala Gln Pro Leu Pro Glu Val Ser Pro Ala Glu Asn Pro
        370                 375                 380
Ala Asn Asn Pro Asn Pro Asn Glu Asn Pro Gly Thr Ser Pro Asn Pro
385                 390                 395                 400
Glu Pro Asp Pro Asp Leu Asn Pro Asp Ala Asn Pro Asp Thr Asp Gly
                405                 410                 415
Gln Pro Gly Thr Arg Pro Asp Ser Pro Ala Val Pro Gly Arg Thr Asn
                420                 425                 430
Gly Arg Asp Gly Lys Asp Gly Lys Asp Gly Lys Asp Gly Gly Leu Leu
        435                 440                 445
Cys Lys Phe Phe Pro Asp Ile Leu Ala Cys Asp Arg Leu Pro Glu Ser
        450                 455                 460
Asn Pro Ala Glu Asp Leu Asn Leu Pro Ser Glu Thr Val Asn Val Glu
465                 470                 475                 480
Phe Gln Lys Ser Gly Ile Phe Gln Asp Ser Ala Gln Cys Pro Ala Pro
                485                 490                 495
Val Thr Phe Thr Val Thr Val Leu Asp Ser Ser Arg Gln Phe Ala Phe
                500                 505                 510
Ser Phe Glu Asn Ala Cys Thr Ile Ala Glu Arg Leu Arg Tyr Met Leu
        515                 520                 525
```

-continued

```
Leu Ala Leu Ala Trp Ala Val Ala Ala Phe Phe Cys Ile Arg Thr Val
    530                 535                 540

Ser Arg Glu Val
545
```